United States Patent [19]

Rembaum

[11] 4,326,008
[45] Apr. 20, 1982

[54] PROTEIN SPECIFIC FLUORESCENT MICROSPHERES FOR LABELLING A PROTEIN

[75] Inventor: Alan Rembaum, Altadena, Calif.

[73] Assignee: California Institute of Technology, Pasadena, Calif.

[21] Appl. No.: 143,838

[22] Filed: Apr. 25, 1980

Related U.S. Application Data

[62] Division of Ser. No. 718,104, Aug. 27, 1976, abandoned.

[51] Int. Cl.$^3$ .................... B32B 5/16; B32B 9/04; G01N 31/00; G01N 33/00
[52] U.S. Cl. .................... 428/403; 428/407; 428/500; 521/56; 260/112.5 R; 260/117; 260/8; 424/8; 424/85; 424/88; 424/12; 252/301.35; 525/54.1; 526/268
[58] Field of Search .................... 521/56; 428/403

[56] References Cited

U.S. PATENT DOCUMENTS

| | | | |
|---|---|---|---|
| 2,500,023 | 3/1946 | Burk | 260/42.21 |
| 3,190,850 | 6/1965 | Burke, Jr. | 260/42.21 X |
| 3,232,691 | 2/1966 | Wilhelm et al. | 8/1 |
| 3,922,232 | 11/1975 | Schein | 260/42.21 |
| 4,100,149 | 7/1978 | Meiller et al. | 428/407 X |
| 4,143,203 | 3/1979 | Rigopulos et al. | 428/403 X |
| 4,181,769 | 1/1980 | Plamondon et al. | 428/407 X |

Primary Examiner—P. Ives
Attorney, Agent, or Firm—Marvin E. Jacobs

[57] ABSTRACT

Highly fluorescent, stable and biocompatible microspheres are obtained by copolymerizing an acrylic monomer containing a covalent bonding group such as hydroxyl, amine or carboxyl, for example, hydroxyethylmethacrylate, with an addition polymerizable fluorescent comonomer such as dansyl allyl amine. A lectin or antibody is bound to the covalent site to provide cell specificity. When the microspheres are added to a cell suspension the marked microspheres will specifically label a cell membrane by binding to a specific receptor site thereon. The labeled membrane can then be detected by fluorescence of the fluorescent monomer.

15 Claims, No Drawings

PROTEIN SPECIFIC FLUORESCENT MICROSPHERES FOR LABELLING A PROTEIN

ORIGIN OF THE INVENTION

The invention described herein was made in the performance of work under a NASA contract and is subject to the provisions of Section 305 of the National Aeronautics and Space Act of 1958, Public Law 83–568 (72 Stat. 435; 42 USC 2457).

This is a division of application Ser. No. 718,104, filed Aug. 27, 1976 now abandoned.

BACKGROUND OF THE INVENTION

1. Field of the Invention

The present invention relates to uniformly-sized, small microspheres, to methods of making the microspheres and to their use in labeling biological cell surfaces.

2. Description of the Prior Art

The isolation and characterization of cell membranes and their components is essential for an understanding of the role in which surface membranes play in regulating a wide variety of biological and immunological activities. The present techniques used for this purpose are not quite satisfactory.

Knowledge of the nature, number and distribution of specific receptors on cell surfaces is of central importance for an understanding of the molecular basis underlying such biological phenomena as cell-cell recognition in development, cell communication and regulation by hormones and chemical transmitters, and differences in normal and tumor cell surfaces. In previous studies, the localization of antigens and carbohydrate residues on the surface of cells, notably red blood cells and lymphocytes, has been determined by bonding antibodies or lectins to such macromolecules as ferritin, hemocyanin or peroxidase which have served as markers for transmission electron microscopy. With advances in high resolution scanning electron microscopy (SEM), however, the topographical distribution of molecular receptors on the surfaces of cell and tissue specimens can be readily determined by similar histochemical techniques using newly developed markers resolvable by SEM.

Recently commercially available polystyrene latex particles have been utilized as immunologic markers for use in the SEM technique. The surface of such polystyrene particles is hydrophobic and hence certain types of macromolecules such as antibodies are absorbed on the surface under carefully controlled conditions. However, such particles stick non-specifically to many surfaces and molecules and this seriously limits their broad application.

The preparation of small, stable spherical particles which are bio-compatible, i.e., do not interact non-specifically with cells or other biological components and which contain functional groups to which specific proteins and other bio-chemical molecules can be covalently bonded is disclosed in copending application Ser. No. 434,124, filed Jan. 17, 1974, now issued on May 18, 1976, as U.S. Pat. No. 3,957,741.

Smaller, more evenly shaped microspheres are disclosed in Ser. No. 634,935, filed Nov. 24, 1975, now issued on Feb. 6, 1979, as U.S. Pat. No. 4,138,383 and microspheres having a density differing from that of cell membranes are disclosed in Ser. No. 634,929, filed Nov. 24, 1975, now issued on July 12, 1977, as U.S. Pat. No. 4,035,316.

The hydroxyl groups can be activated by cyanogen bromide for covalent bonding of proteins and other chemicals containing amino groups to the polymericlatex. Methacrylic acid residues which impart a negative charge onto the particles are likely to prevent non-specific binding to cell surfaces and to provide carboxyl groups to which a variety of bio-chemical molecules can be covalently bonded using the carbodiimide method. Cross-linking of the polymeric matrix is preferable in order to maintain the stability and size of the particles in both aqueous solution and in organic solvents commonly used in the fixation and dehydration of biological specimens for electron or light microscopy.

Microspheres, 150–350 Å in diameter serve as markers for transmission electron microscopy as well as in high resolution scanning electron microscopy. Microspheres larger than 0.2 micron in diameter can be utilized with ordinary visual microscopy. However, the attachment of fluorescent tags to the surface required a covalent bonding reaction and the distribution of tags was not totally uniform and the attachment resulted in a consumption of covalent bonding sites which would otherwise be available for marking with antigen, lectin or antibody.

SUMMARY OF THE INVENTION

Highly fluorescent, stable, biocompatible microspheres are produced in accordance with this invention by addition polymerization of an aqueous dispersion monomer mixture containing an acrylic monomer substituted with a covalent bonding group and an addition polymerizable fluorescent comonomer. Free radicals may be generated by free radical catalysts or by high energy radiation. More uniformly sized and shaped beads are formed from very dilute aqueous monomer systems. Surfactants may be present which aid in steric stabilization and permit the use of relatively high concentration of monomers (up to about 20%).

The microsphere can be utilized to yield a biochemical mapping of the membrane with respect to assessment of surface receptors which can redistribute in the plane of the membrane in response to a matrix containing rigidly displayed ligands. This will be useful in determining the contributing roles of the restriction of movement of certain surface receptors to oncogenic transformation of cells. Other applications include the isolation of differentiated regions of cell surface membranes, and studies of this nature would be of great utility in areas such as development biology.

The microspherical beads containing hydroxyl or amine groups covalently bond to antibodies and other biological materials and are useful as specific cell surface markers for scanning electron microscopy. The particles are found to bind to hormones, toxins, lectins, antibodies, sugars and other molecules and have application in the detection and localization of a variety of cell surface receptors. Particles tagged with fluorescent dye or radioactive molecules serve as sensitive markers for fluorescent microscopy and as reagents for quantitative study of cell surface components. By covalently bonding lectins, antigens, hormones and other molecules to these spheres, detection and localization of specific carbohydrate residues, antibodies, hormone receptors and other specific cell surface components or fragments can also be isolated and determined. These reagents also have application in highly sensitive radioimmune assays, as visual markers for fluorescent and transmission electron microscopy, for radioactive quantitation of specific cell surface receptors and as potential thereapeutic reagents.

The microspheres are hydrophilic, hydrolytically stable, biocompatible and have good mechanical strength. The microspheres are of well characterized structure, of outstanding purity and the hydrophilic properties, size, and mechanical properties can be systematically varied by selection of monomers and polymerization conditions.

These and many other features attendant advantages of the invention will become apparent as the invention becomes better understood by reference to the following detailed description.

DESCRIPTION OF THE PREFERRED EMBODIMENTS

The microspheres are preferably produced by aqueous suspension addition polymerization of a monomer mixture including at least 10%, by weight, of an olefinically unsaturated monomer containing a covalent bonding group such as hydroxyl, carboxyl or amino. Polymerization may be initiated by means of a free radical catalyst such as 0.003 to 0.1 percent by weight of a persulfate such as ammonium persulfate or a peroxide, hydroperoxide or percarbonate.

It is preferred that the aqueous suspension polymerization be conducted in absence of free radical catalyst. Polymerization can proceed by heat alone at temperatures above 50° C. However, it is preferred to conduct the addition polymerization at lower temperature by means of high energy radiation.

The polymerization proceeds with or without stirring with application of high energy radiation capable of generating free radicals in the aqueous system. The radiation source is suitably a cobalt 60 gamma source or cesium source and doses of 0.5 to 1.0 megarads are sufficient for polymerization. The reaction is preferably conducted under oxygen excluding condition, generally by applying vacuum to the reaction vessel or by displacing oxygen gas from the system with an inert gas such as nitrogen. After polymerization has proceeded to completion, the reaction mixture is made neutral by adding acid or base, passed through mixed ion exchange resins to remove emulsifiers. Further purification is achieved by centrifugation on a sucrose gradient.

The addition of 0.05 to 5%, by weight, of a stabilizing agent to the aqueous polymerization system before polymerization is found to further reduce agglomeration. The stabilizing agent is suitably an aqueous soluble polymer such as a polyalkylene oxide polyether or non-ionic surfactants such as Tween which are polyoxyethylene derivatives of fatty acid partial esters of sorbitol, Triton X, or dextrans. The polyethers generally have a molecular weight from 10,000 to 10,000,000, preferably 400,000 to 6,000,000 and are polymers of ethylene oxide, propylene oxide or their mixtures. Polyethylene oxides (PEO) and Triton X are preferred.

Mono-unsaturated covalent bonding monomers are freely water soluble and should comprise from 25–50% of the monomer mixture. These monomers are suitable selected from amino, carboxyl or hydroxyl substituted acrylic monomers. Exemplary monomers are acrylamide (AM), methacrylamide (MAM), acrylic acid, methacrylic acid (MA), dimethylaminomethacrylate or hydroxyl-lower alkyl- or amino-lower-alkyl-acrylates such as those of the formula:

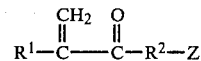

where $R^1$ is hydrogen or lower alkyl of 1–8 carbon atoms, $R^2$ is alkylene of 1–12 carbon atoms, and Z is —OH or $R_3$—N—$R_4$ where $R^3$ or $R^4$ are individually selected from H, lower alkyl, or lower alkoxy of 1–8 carbon atoms. 2-hydroxyethyl methacrylate (HEMA), 3-hydroxypropyl methacrylate and 2-aminoethyl methacrylate are readily available commercially. Porosity and hydrophilicity increase with increasing concentration of monomer.

Inclusion of polyunsaturated compounds also provides cross-linked beads which are less likely to agglomerate. The polyunsaturated compounds are generally present in the monomer mixture in an amount from 0.1–20% by weight, generally 6–12% by weight and are suitably a compatible liquid diene or triene polyvinyl compound capable of addition polymerization with the covalent bonding monomer such as ethylene glycol dimethacrylate, trimethylol propane trimethacrylate, N,N-methylene-bis-acrylamide (BAM), piperazine ethyl methacrylate or divinyl benzene.

For small particle size the monomer mixture preferably contains a large percentage, suitable from 40–70% of sparingly water soluble monomers having hydrophobic characteristics since this is found to result in freely suspended individual small beads. In the absence of such monomers, the particles are of relatively large diameter. The cross-linking agent is sometimes sparingly water soluble. Hydrophobic characteristics can also be provided with monomers such as lower alkyl acrylates suitably methyl methacrylate or ethyl methacrylate or a vinyl pyridine.

Vinyl pyridines suitable for use in the invention are 2-vinyl pyridine, 4-vinyl pyridine and 2-methyl-5-vinyl pyridine. 2-vinyl pyridine has, in general, been found to produce smaller beads, more resistant to agglomeration even in the absence of cross-linking agents and suspending agents.

The fluorescent monomer is present in the monomer mixture in an amount sufficient to provide adequate fluorescence to the microspheres, suitably at least 0.1% to 15% by weight, generally from 1 to 10% by weight thereof. The fluorescent monomer contains a fluorochrome portion to which is attached at least one addition polymerizable group such as an ethylenically unsaturated vinyl or allyl group. Fluorochromes absorb incident radiation, attain an excited state and emit visible light when stimulated by shorter wavelength light. Fluorescence efficiency, the ratio of quanta emitted to quanta absorbed is generally from 0.1 to 0.8 and should not be effected by modification of the fluorochrome molecule necessary to add the olefinic group.

Fluorochromes suitable for conjugation of proteins can readily be converted to addition polymerizable monomers suitable for use in this invention by reaction with an unsaturated compound containing a functional group condensible with the protein conjugation group. For example, fluorochromes containing sulfonic acid or sulfonyl chloride groups can be reacted with amine substituted olefins to form a sulfonamide linkage. The reaction can be generalized as follows:

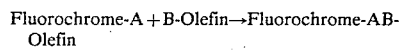

where A is the fluorochrome functional group, B is a cocondensible group and AB is the condensation residue. Suitable A, B, AB pairs follow:

| A | B | AB |
|---|---|---|
| OH | NCO | urethane |
| $NH_2$ | NCO | urea |
| COOH | OH | ester |
| COCl | OH | ester |
| COOH | $NH_2$ | amide |
| COCl | $NH_2$ | amide |
| SCN | $NH_2$ | thiourea |
| $NH_2$ | COOH | amide |
| OH | COOH | ester |
| $SO_3H$ | $NH_2$ | sulfonamide |
| $SO_2Cl$ | $NH_2$ | sulfonamide |

Representative B-Olefin materials are allyl amine, hydroxy or amino alkyl acrylates as previously described, methacrylic anhydride or methacryloyl chloride.

It is also possible to form an adduct of the dye and a difunctional BB compound before reaction with B'-Olefin. For example:

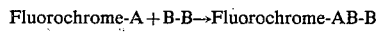

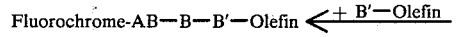

A sulfonyl chloride dye could be reacted with a diamine and then with an unsaturated acyl chloride.

Representative functionally substituted fluorochrome dyes are dansyl chloride (sulfonyl chloride of 1-dimethylaminonaphthalene-5-sulfonic acid), tetramethylrhodamine isothiocyanate (TDIC), fluorescein isothiocyanate (FITC), fluorescamine, RB 200 sulfonyl chloride, fluorescein carbonyl chloride, aminofluorescein, ethidium bromide and the like.

The allyl monomers are difficult to copolymerize by free radical catalysis and the reaction with the functional acrylic monomers may be a grafting addition reaction. Examples of practice follow.

EXAMPLE 1

Dansyl allyl amine, a fluorescent monomer, was synthesized by reacting allyl amine (5 mmol) with dansyl chloride (5 mmol) in acetone (50 cc) in the presence of triethylamine (5 mmol) for 6 hours at 0° C., evaporating to dryness and dissolving the residue in dichloromethane. The solution was washed with sodium bicarbonate solution (3%) and a dilute solution of acetic acid (3%). After drying, it was recrystalized from petroleum ether (mp 81° C.). Its ir spectrum shows a NH stretch at 3280 $cm^{-1}$; olefinic CH at 3000 $cm^{-1}$ and C=C at 1650 $cm^{-1}$.

EXAMPLE 2

Dansylallylamine (DAA) was copolymerized with covalent bonding monomers as follows:

| Material | Weight, g |
|---|---|
| HEMA | 9.0 |
| BAM | 1.0 |
| DAA | 0.1 |
| PEO (M.W. 600,000) | 0.8 |

The monomer system diluted to 200 cc with water was irradiated in a Co-gamma source at room temperature in the absence of air for one hour (0.8 mr) yielded fluorescent particles, the diameter of which was 1.7 microns. The diameter was determined in the presence of water by means of a hemacytometer and photography enlargements of microscope pictures. Impurities and PEO were removed by centrifugation several times in distilled water.

EXAMPLE 3

Fluorescein-allyl amine was formed in situ by addition of the two reactants to the monomer mixture before irradiation.

| Material | Weight, g |
|---|---|
| HEMA | 7.0 |
| MA | 2.0 |
| BAM | 1.0 |
| Allylamine | 0.5 |
| FITC | 0.05 |
| PEO (600,000) | 0.8 |

The monomer system was polymerized into fluorescent microspheres having a diameter of 0.7 microns by the procedure described in Example 2.

Potentiometric titrations indicate that the number of carboxyl groups varies from 1.4 to 2.5 per Å square. Since one carboxyl group would require an area larger than 1 Å square, it is concluded that carboxyl groups are also located inside the microspheres and are accessible to aqueous reagents.

EXAMPLE 4

50 mg of fluorescamine (4-phenylspiro-[furan-2/3H], 1'-phthalan]-3,3' dione) was dissolved in 0.5 g of allylamine, allowed to react over night and evaporated to dryness. The residue was added to 100 c of distilled water containing: 0.4 g of PEO, 1.2 g of HEMA, 0.4 g of methacrylic acid (MA), 1.2 g of acrylamide and 1.2 g of BAM. Nitrogen was passed through the mixture (5 min) which was then irradiated with ionizing radiation from a cobalt-60 source for 3 hours (Total dose: 0.8 megarad). After centrifuging the aqueous suspension and resuspending in water, fluorescent particles were obtained, the average diameter of which was 0.8 microns. The fluorescence intensity was maximum at pH 9 to 10.

EXAMPLE 5

Fluorescent microspheres derivatized with diaminoheptane were coupled to goat antimouse immunoglobulin antibody molecules by a two-step glutaraldehyde reaction, J. Cell Biol. 64, 75 (1975). Murine lymphocytes isolated from a suspension of spleen cells were labeled with the antibody-microsphere conjugates and labeled cells were separated from unlabeled cells by centrifugation. The labeled cells showed strong fluorescence in an ordinary light microscope when illuminated with ultraviolet light.

It is to be realized that only preferred embodiments of the invention have been described and that numerous modifications, substitutions and alterations are all permissable without departing from the spirit or scope of the invention as defined in the following claims.

What is claimed is:

1. A protein specific fluorescent reagent composition for labelling a protein comprising discrete microspheres having a diameter below 100 microns containing a covalent bonding group selected from hydroxyl, amino or carboxyl covalently bound to a conjugate of said protein, said polymer comprising the addition interpolymerized reaction product of a monomer mixture consisting essentially of:

20 to 60% by weight of a first mono-unsaturated acrylic monomer containing at least one of said covalent bonding groups;

0.1% to 15% by weight of a fluorescent comonomer addition polymerizable with said first monomer; and 1 to 20% by weight of a polyunsaturated cross-linking agent addition polymerizable with said first monomer or comonomer.

2. A composition according to claim 1 having a diameter of at least 150 angstrom.

3. A composition according to claim 1 in which the first monomer is selected from acrylamide, hydroxy-lower alkyl acrylates, amino-lower alkyl acrylates, acrylic acid or methacrylic acid.

4. A composition according to claim 3 in which the first monomer is selected from compounds of the formula:

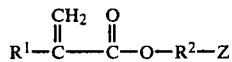

where $R^1$ is hydrogen or lower alkyl of 1-8 carbon atoms, $R^2$ is alkylene of 1-12 carbon atoms, Z is OH or

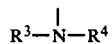

where $R^3$ or $R^4$ are H, lower alkyl or lower alkoxy.

5. A composition according to claim 4 in which the first monomer is selected from 2-hydroxyethyl methacrylate, 3-hydroxypropyl-methacrylate, 2-dimethylaminoethylmethacrylate and 2-aminoethylmethacrylate.

6. A composition according to claim 4 in which the comonomer is Dansyl allyl amine.

7. A composition according to claim 4 in which the comonomer is Fluorescamine allyl amine.

8. A composition according to claim 4 in which the comonomer is Fluorescein allyl amine.

9. A composition according to claim 1 in which the cross-linking agent is a liquid, polyvinyl diene or triene capable of addition polymerization with the first monomer and comonomer and is present in the monomer mixture in an amount from 5–15% by weight.

10. A composition according to claim 9 in which the crosslinking agent is selected from ethylene glycol dimethacrylate, divinyl benzene, trimethylol propane trimethacrylate, and N,N'methylene-bis-acrylamide.

11. A composition according to claim 1 in which the comonomer contains an allyl or vinyl group.

12. A composition according to claim 1 in which the comonomer consists of the condensation linked reaction product of a fluorochrome containing a functional substitution, A and an allyl or vinyl compound containing a functional substitution, B.

13. A composition according to claim 12 in which the comonomer is a compound of the formula:

where AB is the linking condensation residue selected from urethane, urea, ester, amide, thiourea and sulfonamide.

14. A composition according to claim 13 in which the fluorochrome A is selected from dansyl chloride, fluorescamine, RB 200 sulfonyl chloride, fluorescein carbonyl chloride and aminofluorescein.

15. A composition according to claim 14 in which B-Olefin is selected from allyl amine, hydroxy alkyl acrylates, amino alkyl acrylates, methacrylic acid or methacryloyl chloride.

* * * * *